United States Patent [19]

Sasaki et al.

[11] Patent Number: 5,094,990
[45] Date of Patent: Mar. 10, 1992

[54] IRON-ANTIMONY-PHOSPHORUS-CONTAINING METAL OXIDE CATALYST FOR OXIDATION

[75] Inventors: Yutaka Sasaki; Masato Otani; Hiroshi Utsumi; Kazuo Morishita, all of Kanagawa, Japan

[73] Assignee: Nitto Chemical Industry Co., Ltd., Tokyo, Japan

[21] Appl. No.: 540,729

[22] Filed: Jun. 20, 1990

[30] Foreign Application Priority Data

Jun. 23, 1989 [JP] Japan .................................. 1-159457

[51] Int. Cl.$^5$ ................... B01J 27/185; B01J 27/182; B01J 23/18; C01C 3/02
[52] U.S. Cl. ................................. 502/214; 423/376; 502/213
[58] Field of Search ................... 502/209–214

[56] References Cited

U.S. PATENT DOCUMENTS

| 4,511,548 | 4/1985 | Attig et al. | 423/376 |
| 4,946,819 | 8/1990 | Sasaki et al. | 502/214 |
| 4,981,830 | 1/1991 | Sasaki et al. | 502/214 |

FOREIGN PATENT DOCUMENTS

| 0089118 | 9/1983 | European Pat. Off. . |
| 0319192 | 6/1989 | European Pat. Off. . |
| 0323129 | 7/1989 | European Pat. Off. . |
| 0340909 | 11/1989 | European Pat. Off. . |
| 2264528 | 1/1974 | Fed. Rep. of Germany . |
| 2438464 | 2/1975 | Fed. Rep. of Germany . |

*Primary Examiner*—Paul E. Konopka

*Attorney, Agent, or Firm*—Sughrue, Mion, Zinn, Macpeak & Seas

[57] ABSTRACT

An iron-antimony-phosphorus-containing metal oxide catalyst for the catalytic oxidation, comprising a crystalline iron antimonate, the catalyst being represented by the following empirical formula:

$$Fe_aSb_bP_cX_dQ_eR_fO_g(SiO_2)_h$$

wherein X represents at least one element selected from the group consisting of V, Mo and W; Q represents at least one element selected from the group consisting of Li, Na, K, Rb, Cs, Be, Mg, Ca, Sr, Ba, Sc, Y, La, Ce, Pr, Nd, Sm, Th, U, Ti, Zr, Hf, Nb, Ta, Cr, Mn, Re, Co, Ni, Ru, Rh, Pd, Os, Ir, Pt, Cu, Ag, Au, Zn, Cd, Hg, Al, Ga, In, Tl, Ge, Sn and Pb; R represents at least one element selected from the group consisting of B, As, Bi, Se and Te; a, b, c, d, e, f, g and h each is an atomic ratio as follows:

a = about 5 to 15
b = about 5 to 100
c = about 1 to 30
d = about 0 to 10
e = about 0 to 15
f = about 0 to 10
h = about 0 to 300 g is a number of oxygen atom as determined corresponding to the oxides formed by combining the above-mentioned components; the atomic ratio of P/Fe is at least 0.3; the atomic ratio of P/Sb is at least 0.1; and the atomic ratio of P/X is at least 1 when d>0.

10 Claims, No Drawings

IRON-ANTIMONY-PHOSPHORUS-CONTAINING METAL OXIDE CATALYST FOR OXIDATION

FIELD OF THE INVENTION

This invention relates to a metal oxide catalyst containing iron, antimony and phosphorus as essential elements. More particularly, it relates to an iron-antimony-phosphorus containing metal oxide catalyst for oxidation, which has an activity suitable for use in the oxidation reaction of organic compounds and also has physical properties suitable for use as an industrial catalyst. The term "the oxidation reaction of organic compounds" as used herein refers to all normal oxidation reactions, as well as oxidation reactions involving dehydrogenation (oxidative dehydrogenation) and ammoxidation.

BACKGROUND OF THE INVENTION

Metal oxide catalysts containing iron, antimony and phosphorus are known to be useful in production of aldehydes by oxidation of organic compounds, production of dienes, alkenylbenzenes, unsaturated aldehydes or unsaturated acids by oxidative dehydrogenation of organic compounds, and production of nitriles by ammoxidation of organic compounds. For example, ammoxidation of propylene is described in JP-B-38-19111 (the term "JP-B" as used herein refers to an "examined Japanese patent publication"), and U.S. Pat. Nos. 3,542,843, 3,591,620 and 3,988,359; and ammoxidation of methanol is described in JP-B-54-39839, JP-A-1-143643 (corresponding to U.S. patent application Ser. No. 276,586 and European Patent Publication No 319,129A1) (the term "JP-A" as used herein refers to an "unexamined published Japanese patent application"), and U.S. Pat. Nos. 4,511,548 and 4,461,572.

The antimony-containing oxide catalysts which can be used in the reactions stated above involve problems, such as poor reproducibility and operability in the preparation thereof and difficulty in assuring high strength. As a result, some improvements have been made on a process for preparing the catalyst as described in JP-B-46-3456 and JP-B-46-3457, and U.S. Pat. Nos. 3,341,471, 3,657,155 and 3,686,138.

These conventionally proposed processes, however, do not always satisfy both activity and physical properties of the catalyst, and the problem of reproducibility of preparation still remains unsolved. In particular, in the preparation of catalysts having a high phosphorus content as in the catalyst of the present invention, direct application of conventional processes proposed for preparing antimony-containing catalysts fails to attain satisfactory results. For instance, the processes disclosed in U.S. Pat. Nos. 3,657,155 and 3,686,138 are excellent techniques for preparing iron-antimony-containing catalysts suitable for a fluidized bed process. However, it is difficult using these processes to produce catalysts containing a relatively large amount of phosphorus while retaining activity and physical properties for use in a fluidized bed process. This is assumed to be because the presence of a large amount of a phosphorus component not only inhibits oxidation of the antimony but greatly changes the properties of the slurry reducing its stability.

The present inventors had previously found that the activity and physical properties of the catalyst can be improved by adjusting the pH of a slurry during the preparation of the catalyst to not higher than 3 before spray drying when a relatively large amount of phosphorus component is used as a part of raw materials for the catalyst. An improved process described in JP-A-1-171640 (corresponding to European Patent Publication No. 323,129A1) was proposed.

However, it has been found that the proposed process has disadvantages in that a specific component, particularly antimony oxide in the slurry settles out readily, the properties of the slurry are easily changed with the passage of time, the slurry is deposited on the wall of a chamber during spray drying and it is difficult to remove the deposit. Further, the operability during the preparation of the catalyst is poor, for example, the catalyst readily adheres to the vessel during the calcination of the catalyst. In addition, the reproducibility of the catalyst remains unsatisfactory. Particularly, the margin of manufacturing conditions capable of producing a catalyst having physical properties suitable for a fluidized bed reaction is relatively narrow, and the physical properties of the catalyst are greatly varied by a slight change in the preparation conditions of the slurry or in the spray drying conditions of the slurry. Accordingly, the above-described process is not considered to be fully suitable for practical use.

Since the industrial output of products obtained by the oxidation or ammoxidation of organic compounds is high, a slight increase in the yields of the desired products or a slight improvement in the physical properties of the catalyst or catalyst strength gives remarkable commercial and economic effects.

This invention has been performed to improve the activity and physical properties of a catalyst containing iron, antimony and a large amount of phosphorus.

SUMMARY OF THE INVENTION

An object of the present invention is to provide an iron-antimony-phosphorus-containing catalyst for oxidation (including normal oxidation reactions, oxidative dehydrogenation and ammoxidation), which is excellent in catalytic activity as well as in catalyst strength.

Another object of the present invention is to provide an iron-antimony-phosphorus-containing catalyst for oxidation, which can be produced with good reproducibility.

Still another object of the present invention is to provide an iron-antimony-phosphorus-containing catalyst for oxidation, which is suitable for use in the production of acrylonitrile, methacrylonitrile and hydrogen cyanide.

It has now been found that these and other objects of the invention are attained by an iron-antimony-phosphorus-containing metal oxide catalyst for oxidation which is a metal oxide catalyst containing iron, antimony and phosphorus and containing a crystalline iron antimonate, represented by the following empirical formula:

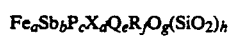

$$Fe_a Sb_b P_c X_d Q_e R_f O_g (SiO_2)_h$$

wherein X is at least one element selected from the group consisting of V, Mo and W; Q is at least one element selected from the group consisting of Li, Na, K, Rb, Cs, Be, Mg, Ca, Sr, Ba, Sc, Y, La, Ce, Pr, Nd, Sm, Th, U, Ti, Zr, Hf, Nb, Ta, Cr, Mn, Re, Co, Ni, Ru, Rh, Pd, Os, Ir, Pt, Cu, Ag, Au, Zn, Cd, Hg, Al, Ga, In, Tl, Ge, Sn and Pb; and R is at least one element selected from the group consisting of B, As, Bi, Se and Te; a, b, c, d, e, f, g and h each is an atomic ratio, wherein a = about 5 to 15, b = about 5 to 100, c = about 1 to 30, d = about 0 to 10, e = about 0 to 15, f = about 0 to 10, g = a number of oxygen atoms as determined corresponding to the oxides formed by combining the above-mentioned components and h = about 0 to 300; and the atomic ratio of P/Fe is at least 0.3, the atomic ratio of P/Sb is at least 0.1; and the atomic ratio of P/X is at least 1 when d > 0.

DETAILED DESCRIPTION OF THE INVENTION

In the catalyst of the present invention, each component of Fe, Sb and P must be blended in the range defined above and iron antimonate must be present in a crystalline form. In the above formula, Q is preferably at least one element selected from the group consisting of Li, Na, K, Rb, Cs, Mg, Ca, La, Ce, Ti, Zr, Nb, Ta, Cr, Mn, Re, Co, Ni, Cu, Ag, Zn, Al, Sn and Pb; R is preferably at least one element selected from the group consisting of B, Bi, and Te; b is preferably 10 to 60, and c is preferably 3 to 20. When the ratio of the Fe component is lower than the above-described lower limit, catalyst activity is lowered, while when the ratio is higher than the upper limit, the selectivity of the desired product is lowered. When the ratio of the Sb component is lower than the above-described lower limit, the selectivity of the desired product is lowered, while when the ratio is higher than the upper limit, catalyst activity is lowered and physical properties become poor. When the ratio of the P component is lower than the above-described lower limit, the selectivity of the desired product is lowered, while when the ratio is higher than the upper limit, catalyst activity is lowered and a deterioration in physical properties due to the formation of antimony phosphate is found. Also, various problems occur on the production of catalysts. For example, the catalyst adheres during the calcination of the catalyst to cause a caking. Further, when crystalline iron antimonate is not found in the catalyst, the yield of the desired product is low and the physical properties of the catalyst become poor, for example, catalyst strength is lowered even when the ratios of Fe, Sb and P components are in the range defined above.

Several iron antimonates such as $FeSbO_4$, $FeSb_2O_4$, $FeSb_2O_6$ and $FeSb_5O_{12}$ are known, and $FeSbO_4$ is generally known. The invention includes any known iron antimonate, but the iron antimonate in the catalyst of the present invention preferably includes $FeSbO_4$. The structure of iron antimonate is known by X-ray diffraction data as described, for example, in J. Korinth, P. Royen, *Z. anorg. allg. Chem.* 340, 146–157 (1965).

The presence of crystalline iron antimonate in the catalyst of the present invention can be confirmed by X-ray diffraction. The term "crystalline iron antimonate" as used herein refers to not only pure iron antimonate, but also iron antimonate in the form of a solid solution containing various elements dissolved therein. Further, it is not necessary that all of the Fe component and the Sb component form crystalline iron antimonate. A part of the Fe component or the Sb component may exist in the free form or in the form of other compounds.

The catalyst of the present invention contains iron, antimony and phosphorus as essential elements and crystalline iron antimonate in such a proportion that P/Fe is at least 0.3, preferably 0.3 to 3 by atomic ratio and P/Sb is at least 0.1, preferably 0.15 to 3, more preferably 0.2 to 2 by atomic ratio.

Optional components other than iron, antimony and phosphorus can be used by properly choosing them according to the selectivity of the desired product, reaction rate, the physical properties of the catalyst, etc. For example, the X component is used in such a proportion that P/X is at least 1, preferably 1 to 100, more preferably 1 to 40 by atomic ratio, whereby the reaction rate can be increased. The Q component has the effect of improving physical properties and controlling the formation of by-products, and the R component has an effect of improving selectivity.

The catalyst of the present invention can be used without a carrier, but it is preferred that the catalyst is supported on an appropriate carrier. Examples of the carrier include silica, alumina, silica-alumina, titania, silica-titania, and zirconia. Silica is particularly preferred.

The catalyst of the present invention can be prepared by preparing a slurry, preferably an aqueous slurry, containing crystalline iron antimonate, a phosphorus component and optionally at least one component selected from the group consisting of the X component, Q component, R component and Si component, drying the slurry and calcining the resulting dried material.

The iron antimonate can be prepared by various methods.

When the iron antimonate is prepared in the slurry state, an aqueous slurry containing an iron compound such as iron nitrate and an antimony compound such as antimony trioxide is heat-treated. It is preferred that the heat treatment is carried out while retaining the form of the slurry with uniform stirring. The heating temperature is about 40° to about 150° C., preferably about 80° to about 100° C. for from about 10 minutes to 50 hours. Preferably, the pH of the slurry is adjusted to not higher than about 7, preferably about 1 to about 4 before heat treatment.

When the iron antimonate is prepared by calcination, the calcination of the mixture of an iron compound and an antimony compound is carried out at a temperature of 300° to 1000° C., preferably 500° to 950° C. for 0.5 to 50 hours.

Examples of the iron compound which can be used as the starting material include iron oxides such as ferrous oxide, ferric oxide and tri-iron tetroxide; iron salts of inorganic acids such as ferrous chloride, ferric chloride, iron nitrate and iron carbonate; and iron salts of organic acids such as iron oxalate and iron citrate.

Examples of the antimony compound include antimony trioxide, antimony tetroxide, antimony pentoxide, antimonic acid, polyantimonic acid, sodium antimonate, potassium antimonate, antimony trichloride and antimony pentachloride.

It can easily be confirmed by X-ray diffraction whether the crystalline iron antimonate is formed or not.

A slurry, preferably an aqueous slurry, containing the thus-obtained crystalline iron antimonate, a phosphorus compound and optionally at least one member selected from the group consisting of raw materials for X, Q, R and Si components is formed. The raw materials for X, Q, R and Si components may be mixed with an aqueous slurry containing an iron compound and an antimony compound in the preparation of the iron antimonate. Subsequently, the slurry is dried and calcined to obtain an active catalyst. The calcination is generally carried out at a temperature of about 200° to about 950° C., preferably about 550° to about 900° C. in air. The calcination time is about 0.5 to about 50 hours. It is preferred that the phosphorus compound is mixed with the crystalline iron antimonate prepared in the manner described above. When the phosphorus compound is present from the start of the reaction of the iron compound with the antimony compound in an aqueous slurry to prepare the iron antimonate, the iron antimonate is not formed, even when the reaction mixture is treated under predetermined conditions (pH, temperature, etc.). This is because the phosphorus compound prevents the reaction for the formation of the iron antimonate from proceeding. When a slurry containing no iron antimonate is used as mentioned above, the slurry is liable to form precipitates, and operability is poor. For example, large amounts of deposits are formed in the chamber during spray drying, and there is a difficulty in preparing a catalyst excellent in activity and strength with good reproducibility, as shown in Comparative Examples 1 and 7 described hereinafter. Accordingly, the iron antimonate must be present in the slurry containing catalyst components to obtain the catalyst of the present invention.

Examples of a material for the phosphorus component include orthophosphoric acid, condensed phosphoric acid, phosphorus pentoxide, diammonium hydrogenphosphate, ammonium dihydrogenphosphate and ammonium phosphate.

Silica sol can be advantageously used as the raw material for silica carrier. However, white carbon, fumed silica or silica hydrogel can be used as a part or all of the raw material.

When elements represented by X, Q and R in the empirical formula are introduced as optional components into the catalyst, the starting materials of these elements are used in the form of nitrates, carbonates, sulfates, hydroxides, oxides or other compounds.

The catalyst of the present invention can be used for fixed bed and fluidized bed reactors.

When a catalyst for use in the fixed bed is to be produced, an aqueous slurry containing the crystalline iron antimonate, the phosphorus compound and other materials for other catalyst components is dried or dried and calcined, and the resulting material is molded by means of pelletizing, or extrusion.

When a catalyst for use in the fluidized bed is to be produced, it is preferred that the aqueous solution or slurry is spray-dried to form fine spherical particles. The spray drying of the slurry can be carried out by using any conventional spray drier such as a rotary disc type, high-pressure nozzle type or two-fluid nozzle type drier. Fluidized bed calciners can be used for calcination.

The above-described process for producing the catalyst is suitable for use in the production of a catalyst for the fluidized bed in particular, and a catalyst excellent in activity as well as in strength can be obtained with good reproducibility.

The catalyst of the present invention is suitable for use in conventional reactions such as the oxidation, oxidative dehydrogenation and ammoxidation of organic compounds. A mixed gas of a starting organic compound, oxygen and optionally ammonia in a molar ratio of organic compound:oxygen:ammonia = 1:0.3 to 15: 0.5 to 7 is passed through a reactor packed with the catalyst at a temperature of 200° to 600° C. Contact time is preferably 0.05 to 20 seconds, and reaction pressure is preferably atmospheric pressure to 2 kg/cm$^2$ G.

The reaction may be carried out in the fixed bed or fluidized bed, but the fluidized bed is preferable.

The catalyst of the present invention displays excellent performance when used in the oxidation, oxidative dehydrogenation or ammoxidation of organic compounds such as olefinic hydrocarbons, alcohols, aldehydes and alkyl-substituted aromatic hydrocarbons. Particularly, the catalyst of the present invention is suitable for use in the production of hydrogen cyanide by the ammoxidation of methanol. Reaction conditions are such that the molar ratio of oxygen/methanol in the feed gas is 0.5 to 15, preferably 1 to 10, the molar ratio of ammonia/methanol is 0.5 to 3, preferably 0.7 to 2.5, reaction temperature is 350° to 500° C., contact time is 0.1 to 20 seconds and reaction pressure is atmospheric pressure to 2 kg/cm$^2$G.

It is difficult to obtain a catalyst having satisfactory good strength with good reproducibility by a conventional method for producing a catalyst, wherein the phosphoric component and the antimony component are present from the start of mixing and calcined as described in JP-A-1-171640 (corresponding to European Patent Publication No. 323,129A1). In conventional process, the properties of the catalyst slurry are liable to be changed with the passage of time, the activity and physical properties of the catalyst are relatively greatly varied. Hence the process has a serious problem with regard to reproducibility and disadvantages in that various problems occur on an industrial production scale, for example, large amounts of deposits are formed on the wall of the spray drier and operability is poor.

On the other hand, a catalyst excellent in activity as well as in physical properties can be obtained with good reproducibility according to the present invention. Further, operability is good during the production of the catalyst.

The present invention is now illustrated in greater detail with reference to the following examples which, however, are not to be construed as limiting the invention in any way. Unless otherwise indicated, all parts, percent and ratios are by weight.

Test for Activity of Catalyst

Activity test was carried out in the following manner. The starting organic compound, air and ammonia were passed through the catalyst bed of a fluidized bed reactor (the inner diameter of the fluidized zone of the catalyst being 2.5 cm and the height thereof being 40 cm). Reaction pressure was atmospheric pressure.

The conversion of the starting organic compound and the yield and selectivity of the desired product in the examples and comparative examples were determined by the following definitions.

$$\text{Conversion (\%)} = \frac{\text{Weight (g) of carbon in starting compound consumed by reaction}}{\text{Weight (g) of carbon in starting compound fed}} \times 100$$

$$\text{Yield (\%)} = \frac{\text{Weight (g) of carbon in desired product formed}}{\text{Weight (g) of carbon in starting compound fed}} \times 100$$

$$\text{Selectivity (\%)} = \frac{\text{Weight (g) of carbon in desired product formed}}{\text{Weight (g) of carbon in starting compound consumed by reaction}} \times 100$$

Activity test conditions were as follows:

(1) Ammoxidation of methanol $O_2$ (fed as air)/methanol = 4.3 (mol/mol) $NH_3$/methanol = 1.1 (mol/mol)
(2) Ammoxidation of propylene $O_2$ (fed as air)/propylene = 2.15 (mol/mol) $NH_3$/propylene = 1.1 (mol/mol)
(3) Ammoxidation of isobutene $O_2$ (fed as air)/isobutene = 2.3 (mol/mol) $NH_3$/isobutene = 1.2 (mol/mol)

Test for Strength of Catalyst
Attrition resistance test

The test was carried out according to the method described in Test Methods for Synthetic Catalytic Cracking Catalyst, American Cyanamid Co. Ltd. 6/31-4 m-1/57, a well-known test method for fluid catalytic cracking catalysts.

Attrition loss (%) R wa determined by the following formula.

$$\text{Attrition loss (\%) } R = \frac{B}{C - A} \times 100$$

wherein
A = Weight (g) of catalyst lost by attrition during a period of the first 5 hours.
B = Weight (g) of catalyst lost by attrition during a period of 20 hours after the lapse of the first 5 hours.
C = Weight (g) of catalyst fed to test.

The test was conducted with C = 50 g. The higher the attrition resistance of the catalyst, that is, the higher the strength of the catalyst, the smaller the value of attrition loss (%) R.

EXAMPLE 1

A catalyst having the empirical formula $$Fe_{13}Sb_{25}P_6O_{84.5}(SiO_2)_{60}$$

was prepared in the following manner.
(I) 273.5 g of antimony trioxide powder was weighed.
(II) 420 ml of nitric acid (specific gravity: 1.38) was mixed with 530 ml of water, the mixture was heated and 54.5 g of electrolytic iron powder was added portionwise thereto to dissolve it.
(III) 1354 g of silica sol (20 wt % $SiO_2$) was weighed.
(III) and (I) in this order were added to (II) while stirring well. The pH of the mixture was adjusted to 2 by adding 15% ammonia water.
The resulting slurry was heated at 98° C. with stirring for 3 hours.
The solid in the slurry was examined by X-ray diffractometry and it was found that crystalline iron antimonate was formed.
(IV) 52.0 g of phosphoric acid (85 wt %) was weighed.
Phosphoric acid (IV) was added to the aqueous slurry containing the above crystalline iron antimonate and the mixture was thoroughly stirred for 1 hour. The thus-obtained aqueous slurry containing the crystalline iron antimonate, the phosphorus compound and the silica carrier material was spray-dried by using a rotary disc type spray drier. The resulting fine spherical particles (average particle diameter: about 50 μ) were calcined at 200° C. for 2 hours, at 400° C. for 3 hours and then at 800° C. for 3 hours.

EXAMPLE 2

A catalyst having the same empirical formula as that of the catalyst of Example 1 was prepared in the following manner.
(I) 273.5 g of antimony trioxide powder was weighed.
(II) 394.4 g of ferric nitrate was weighed.
(I) was thoroughly mixed with (II) and the mixture was calcined at 550° C. for one hour and at 600° C. for 2 hours. 381 g of water was added thereto and the mixture was crushed in a ball mill in a wet process for 15 hours.
The solid in the slurry was examined by X-ray diffractometry and it was found that crystalline iron antimonate was formed.
(III) 1354 g of silica sol (20 wt % $SiO_2$) was weighed.
(IV) 52.0 g of phosphoric acid (85 wt %) was weighed.
The aqueous slurry containing the above crystalline iron antimonate was mixed with silica sol (III). Phosphoric acid (IV) was added thereto and the mixture was thoroughly stirred for 1 hour. The thus-obtained aqueous slurry containing the crystalline iron antimonate, the phosphorus compound and the silica carrier material was spray-dried by using a rotary disc type spray drier. The resulting fine spherical particles (average particle diameter: about 50μ) were calcined at 200° C. for 2 hours, at 400° C. for 3 hours and then at 800° C. for 3 hours.

EXAMPLE 3

A catalyst having the empirical formula $$Fe_{13}Sb_{20}P_{12}V_{0.5}Cu_1O_{91.75}(SiO_2)_{30}$$

was prepared in the same manner as in Example 1 except that each of ammonium metavanadate as the raw material for V and copper nitrate as the raw material for Cu was dissolved in pure water and added after the addition of antimony trioxide.

EXAMPLE 4

A catalyst having the empirical formula $$Fe_8Sb_{25}Phd 13Mo_{0.3}V_{0.3}Mg_5Cu_2O_{96.15}(SiO_2)_{80}$$

was prepared in the same manner as in Example 1 except that each of ammonium paramolybdate as the raw material for Mo, ammonium metavanadate as the raw material for V, magnesium nitrate as the raw material for Mg and copper nitrate as the raw material for Cu was dissolved in pure water and added after the addition of antimony trioxide.

EXAMPLE 5

A catalyst having the empirical formula $$Fe_{11}Sb_{25}P_{15}Mo_{0.5}W_{0.2}Mn_2Co_1O_{111.1}(SiO_2)_{60}$$

was prepared in the same manner as in Example 1 except that each of ammonium paramolybdate as the raw material for Mo, ammonium paratungstate as the raw material for W, manganese nitrate as the raw material for Mn and cobalt nitrate as the raw material for Co was dissolved in pure water and added after the addition of antimony trioxide.

EXAMPLE 6

A catalyst having the empirical formula $Fe_{10}Sb_{20}P_{10}Mo_{0.2}V_{0.3}Ni_2Cu_2Te_{0.1}O_{85.55}(SiO_2)_{60}$ was prepared in the same manner as in Example 1 except that each of ammonium metavanadate as the raw material for V, ammonium paramolybdate as the raw material for Mo, nickel nitrate as the raw material for Ni, copper nitrate a the raw material for Cu and telluric acid as the raw material for Te was dissolved in pure water and added after the addition of antimony trioxide.

EXAMPLE 7

A catalyst having the empirical formula $Fe_{10}Sb_{25}P_8Mo_1Sn_2Ag_{0.1}Cr_{0.2}Ce_{0.1}O_{92.6}(SiO_2)_{60}$ was prepared in the same manner as in Example 1 except that each of ammonium paramolybdate as the raw material for Mo, the product obtained by oxidizing metallic tin powder with nitric acid as the raw material for Sn, silver nitrate as the raw material for Ag, chromium nitrate as the raw material for Cr and ammonium cerium nitrate as the raw material for Ce was dissolved or suspended in pure water and added after the addition of antimony trioxide.

EXAMPLE 8

A catalyst having the empirical formula $Fe_{12}Sb_{20}P_4Mo_{1.5}Bi_{1.0}Pb_{0.1}O_{74.2}(SiO_2)_{60}$ was prepared in the same manner as in Example 1 except that each of ammonium paramolybdate as the raw material for Mo, bismuth nitrate as the raw material for Bi and lead nitrate as the raw material for Pb was dissolved or suspended in pure water and added after the addition of antimony trioxide.

EXAMPLE 9

A catalyst having the empirical formula $Fe_{13}Sb_{40}P_{10}V_{0.5}Mo_{0.1}Zn_3B_{0.5}Na_{0.1}Li_{0.1}O_{129.9}(SiO_2)_{60}$ was prepared in the same manner as in Example 1 except that each of ammonium metavanadate as the raw material for V, ammonium paramolybdate as the raw material for Mo, zinc nitrate as the raw material for Zn, boric anhydride as the raw material for B, sodium nitrate as the raw material for Na and lithium nitrate as the raw material for Li was dissolved in pure water and added after the addition of antimony trioxide.

EXAMPLE 10

A catalyst having the empirical formula $Fe_6Sb_{15}P_7Mo_{0.1}V_{0.3}Al_2K_{0.2}Bi_{0.5}O_{61.4}(SiO_2)_{30}$ was prepared in the same manner as in Example 1 except that each of ammonium paramolybdate as the raw material for Mo, ammonium metavanadate as the raw material for V, aluminum nitrate as the raw material for Al, potassium nitrate as the raw material for K and bismuth nitrate as the raw material for Bi was dissolved or suspended in pure water and added after the addition of antimony trioxide.

EXAMPLE 11

A catalyst having the empirical formula $Fe_7Sb_{10}P_{20}Ti_1La_{0.5}O_{83.25}(SiO_2)_{50}$ was prepared in the same manner as in Example 1 except that each of titanium dioxide as the raw material for Ti, and lathanum nitrate as the raw material for La was dissolved or suspended in pure water and added after the addition of antimony trioxide.

EXAMPLE 12

A catalyst having the empirical formula $Fe_{10}Sb_7P_8Mo_{0.3}Zr_{0.5}Re_{0.3}B_1Bi_2O_{56.3}(SiO_2)_{50}$ was prepared in the same manner as in Example 1 except that each of ammonium paramolybdate as the raw material for Mo, zirconium oxynitrate as the raw material for Zr, and rhenium oxide as the raw material for Re, boric acid as the raw material for B, bismuth nitrate as the raw material for Bi was dissolved or suspended in pure water and added after the addition of antimony trioxide.

EXAMPLE 13

A catalyst having the empirical formula $Fe_{13}Sb_{25}P_{10}Mo_{0.1}V_{0.5}Cu_3O_{99.05}(SiO_2)_{60}$ was prepared in the the following manner.
(I) 286.7 g of antimony trioxide was weighed.
(II) 15.0 g of electrolytic copper was added to 40 ml of nitric acid (specific gravity: 1.38) and completely dissolved therein. The resulting copper nitrate solution was diluted with 530 ml of pure water. 57.1 g of electrolytic iron powder was added thereto to dissolve it in said solution.
(III) 1418.3 g of silica sol (20 wt % $SiO_2$) was weighed.
(IV) 1.39 g of ammonium paramolybdate was weighed and dissolved in 50 ml of pure water.
(V) 4.6 g of ammonium metavanadate was weighed and dissolved in 15 ml of 35% hydrogen peroxide solution and 50 ml of pure water.
(VI) 90.7 g of phosphoric acid (85 wt %) was weighed.

Silica sol (III) was added to the iron nitrate-copper nitrate solution (II). Subsequently, (I), (IV) and (V) in that order were added thereto and the mixture was thoroughly stirred for 0.5 hour.

Aqueous ammonia (15 wt %) was added thereto with stirring to adjust the pH of the mixture to 2, and the mixture was heated at 100° C. for 4 hours.

It was found that crystalline iron antimonate was formed in the heat-treated slurry. Phosphoric acid (VI) was added thereto and the slurry was thoroughly stirred for 1 hour and spray-dried by using a rotary disc type spray drier. The resulting fine spherical particles (average particle diameter: about 50μ) were calcined at 200° C. for 2 hours and at 500° C. for 2 hours.

COMPARATIVE EXAMPLE 1

A catalyst having the same empirical formula as that of the catalyst of Example 1 was prepared in the following manner.

(I) 273.5 g of antimony trioxide was weighed.

(II) 420 ml of nitric acid (specific gravity: 1.38) was mixed with 530 ml of pure water and the mixture was heated to 80° C. 54.5 g of electrolytic iron powder was added portionwise thereto and dissolved therein.

(III) 1354 g of silica sol (20 wt % $SiO_2$) was weighed.

(IV) 52.0 g of phosphoric acid (85 wt %) was weighed. (III), (IV) and (I) in this order were added to (II). The mixture was thoroughly stirred and heat-treated at 100° C. for one hour. Solids in the slurry were examined by X-ray diffractometry and it was found that iron antimonate was not formed. Further, when the slurry was left to stand, antimony trioxide powder was immediately precipitated. While stirring the slurry, it was spray-dried by using a rotary disc type spray drier. A large amount of the slurry was deposited on the wall of the spray drier in comparison with Example 1. The deposit adhered firmly to the wall so that there was a difficulty in removing the deposit. The resulting fine spherical particles (average particle diameter: about 50μ) were calcined at 200° C. for 2 hours, at 400° C. for 3 hours and then at 800° C. for 3 hours.

It was found that crystalline iron antimonate was present in the calcined catalyst. However, the catalyst strength was low and the yield of the desired product (hydrogen cyanide) was also low in comparison with the catalyst of Example 1 wherein the iron antimonate was formed in the slurry before spray drying.

COMPARATIVE EXAMPLE 2

A catalyst having the same composition as that of the catalyst of Example 1 was prepared in the following manner.

(I) 273.5 g of antimony trioxide was weighed.

(II) 77.9 g of iron trioxide was weighed.

(III) 1354 g of silica sol (20 wt % $SiO_2$) was weighed.

(IV) 52.0 g of phosphoric acid (85 wt %) was weighed.

(I), (II) and (IV) in order were added to (III) and the mixture was thoroughly stirred.

It was found that iron antimonate was not formed in the resulting slurry. The slurry was spray-dried by using a rotary disc type spray drier. The resulting fine spherical particles (average particle diameter: about 50μ) were calcined at 200° C. for 2 hours, at 400° C. for 3 hours and then at 800° C. for 3 hours. The resulting catalyst was examined by X-ray diffractometry and it was found that iron antimonate was not formed.

COMPARATIVE EXAMPLE 3

A catalyst having the empirical formula

$Fe_{11}P_{15}Mo_{0.5}W_{0.2}Mn_2Co_1O_{61.1}(SiO_2)_{60}$ was prepared in the same way as in Example 5 except that the Sb component was omitted.

COMPARATIVE EXAMPLE 4

A catalyst having the empirical formula

$Sb_{25}P_{15}Mo_{0.5}W_{0.2}Mn_2Co_1O_{94.6}(SiO_2)_{60}$ was prepared in the same way as in Example 5 except that the Fe component was omitted.

COMPARATIVE EXAMPLE 5

A catalyst having the empirical formula

$Fe_{11}Sb_{25}Mo_{0.5}W_{0.2}Mn_2Co_1O_{73.6}(SiO_2)_{60}$ was prepared in the same way as in Example 5 except that the P component was omitted.

COMPARATIVE EXAMPLE 6

A catalyst (having the same composition as that of the catalyst of Example 13) having the empirical formula

$Fe_{13}Sb_{25}P_{10}Mo_{0.1}V_{0.5}Cu_3O_{99.05}(SiO_2)_{60}$ was prepared in the following manner.

(I) 286.7 g of antimony trioxide was weighed.

(II) 15 g of electrolytic copper was added to 420 ml of nitric acid (specific gravity: 1.38) and completely dissolved therein. The resulting copper nitrate solution was diluted with 530 ml of pure water. 57.1 g of electrolytic iron powder was added thereto and dissolved therein.

(III) 1418.3 g of silica sol (20 wt % $SiO_2$) was weighed.

(IV) 1.39 g of ammonium paramolybdate was dissolved in 50 ml of pure water.

(V) 4.6 g of ammonium metavanadate was dissolved in a mixed solution of 15 ml of 35% hydrogen peroxide solution and 50 ml of water.

(VI) 90.7 g of phosphoric acid (85 wt %) was weighed.

Silica sol (III) was added to the iron nitrate-copper nitrate solution (II). Subsequently, (I), (IV), (V) and (VI) in that order were added thereto and the mixture was thoroughly stirred and heated at 100° C. for one hour. It was found that iron antimonate was not formed in the resulting slurry. The slurry was spray-dried in a conventional manner by using a rotary disc type spray drier. The resulting fine particles (average particle diameter: about 50μ) were calcined at 200° C. for 2 hours and at 500° C. for 2 hours in the same manner as in Example 13.

The resulting catalyst had the same composition as that of the catalyst of Example 13. Further, the calcination conditions of this Example were the same as those of Example 13. However, X-ray diffraction indicated that iron antimonate was not formed. Furthermore, the yield of the desired product (hydrogen cyanide) was very low in comparison with the catalyst of Example 13 wherein the catalyst was prepared by previously forming the iron antimonate.

Accordingly, it will be understood that the presence of the iron antimonate in the catalyst is an important factor.

The activity tests of the catalysts obtained in Examples 1 to 13 and Comparative Examples 1 to 6 were carried out.

The results are shown in Table 1

TABLE 1

| | Catalyst Composition (Atomic Ratio) | Final Calcining Temp. (°C.) | Rough Bulk Density (g/ml) | Iron Antimonate in Catalyst | Activity Test Condition | | |
|---|---|---|---|---|---|---|---|
| | | | | | Reaction | Reaction Temp. (°C.) | Contact Time (sec) |
| Ex. 1 | $Fe_{13}Sb_{25}P_6O_{84.5}(SiO_2)_{60}$ | 800 | 1.12 | formed | (1) | 420 | 1.5 |
| Ex. 2 | $Fe_{13}Sb_{25}P_6O_{84.5}(SiO_2)_{60}$ | 800 | 1.05 | " | (1) | 420 | 1.5 |
| Ex. 3 | $Fe_{13}Sb_{20}P_{12}V_{0.5}Cu_1-O_{91.75}(SiO_2)_{30}$ | 810 | 1.23 | " | (1) | 410 | 2.0 |
| Ex. 4 | $Fe_8Sb_{25}P_{13}Mo_{0.3}V_{0.3}-Mg_5Cu_2O_{96.15}(SiO_2)_{80}$ | 850 | 1.02 | " | (1) | 420 | 2.0 |
| Ex. 5 | $Fe_{11}Sb_{25}P_{15}Mo_{0.5}W_{0.2}-Mn_2Co_1O_{111.1}(SiO_2)_{60}$ | 850 | 1.15 | " | (1) | 415 | 1.5 |
| Ex. 6 | $Fe_{10}Sb_{20}P_{10}Mo_{0.2}V_{0.3}-Ni_2Cu_2Te_{0.1}O_{85.55}(SiO_2)_{60}$ | 700 | 1.17 | " | (1) | 410 | 1.0 |
| Ex. 7 | $Fe_{10}Sb_{25}P_8Mo_1Sn_2Ag_{0.1}-Cr_{0.2}Ce_{0.1}O_{92.6}(SiO_2)_{60}$ | 750 | 1.18 | " | (3) | 430 | 2.0 |
| Ex. 8 | $Fe_{12}Sb_{20}P_4Mo_{1.5}Bi_{1.0}-Pb_{0.1}O_{74.2}(SiO_2)_{60}$ | 700 | 1.15 | " | (2) | 460 | 5.0 |
| Ex. 9 | $Fe_{13}Sb_{40}P_{10}V_{0.5}Mo_{0.1}-Zn_3B_{0.5}Na_{0.1}Li_{0.1}O_{129.9}(SiO_2)_{60}$ | 800 | 1.18 | " | (1) | 420 | 2.0 |
| Ex. 10 | $Fe_6Sb_{15}P_7Mo_{0.1}V_{0.3}Al_2-K_{0.2}Bi_{0.5}O_{61.4}(SiO_2)_{30}$ | 800 | 1.15 | formed | (1) | 410 | 1.5 |
| Ex. 11 | $Fe_7Sb_{10}P_{20}Ti_1La_{0.5}-O_{83.25}(SiO_2)_{50}$ | 650 | 1.01 | " | (1) | 415 | 2.5 |
| Ex. 12 | $Fe_{10}Sb_7P_8Mo_{0.3}Zr_{0.5}-Re_{0.3}B_1Bi_2O_{56.3}(SiO_2)_{50}$ | 750 | 0.97 | " | (1) | 410 | 1.5 |
| Ex. 13 | $Fe_{13}SB_{25}P_{10}Mo_{0.1}V_{0.5}-Cu_3O_{99.05}(SiO_2)_{60}$ | 500 | 1.12 | " | (1) | 390 | 0.5 |
| Comp. Ex. 1 | $Fe_{13}Sb_{25}P_6O_{84.5}(SiO_2)_{60}$ | 800 | 1.02 | formed | (1) | 420 | 1.5 |
| Comp. Ex. 2 | $Fe_{13}Sb_{25}P_6O_{84.5}(SiO_2)_{60}$ | 800 | 0.89 | not formed | (1) | 420 | 1.5 |
| Comp. Ex. 3 | $Fe_{11}P_{15}Mo_{0.5}W_{0.2}Mn_2-Co_1O_{61.1}(SiO_2)_{60}$ | 850 | 0.88 | " | (1) | 415 | 1.5 |
| Comp. Ex. 4 | $Sb_{25}P_{15}Mo_{0.5}W_{0.2}Mn_2-Co_1O_{94.6}(SiO_2)_{60}$ | 850 | 0.85 | " | (1) | 415 | 1.5 |
| Comp. Ex. 5 | $Fe_{11}Sb_{25}Mo_{0.1}W_{0.2}Mn_2-Co_1O_{73.6}(SiO_2)_{60}$ | 850 | 0.94 | formed | (1) | 415 | 1.5 |
| Comp. Ex. 6 | $Fe_{13}Sb_{25}P_{10}Mo_{0.1}V_{0.5}-Cu_3O_{99.05}(SiO_2)_{60}$ | 500 | 1.03 | not formed | (1) | 390 | 0.5 |

| | Result of Activity Test | | | |
|---|---|---|---|---|
| | Yield of Desired Product* (%) | Conversion of Starting Material* (%) | Selectivity of Desired Product* (%) | Attrition Loss (%)R |
| Ex. 1 | hydrogen cyanide 92.1 | methanol 98.6 | hydrogen cyanide 93.4 | 0.8 |
| Ex. 2 | 91.8 | 97.1 | 94.5 | 1.1 |
| Ex. 3 | 92.5 | 100 | 92.5 | 0.5 |
| Ex. 4 | 93.1 | 97.3 | 95.7 | 0.6 |
| Ex. 5 | 93.4 | 99.8 | 93.6 | 0.5 |
| Ex. 6 | 93.6 | 99.7 | 93.8 | 0.5 |
| Ex. 7 | methacrylonitrile 68.2 | isobutene 97.6 | methacrylonitrile 69.8 | 0.7 |
| Ex. 8 | acrylonitrile 72.1 | propylene 94.3 | acrylonitrile 76.5 | 0.5 |
| Ex. 9 | hydrogen cyanide 93.1 | methanol 98.5 | hydrogen cyanide 94.5 | 0.6 |
| Ex. 10 | 93.3 | 99.5 | 93.8 | 0.5 |
| Ex. 11 | 88.9 | 97.8 | 90.9 | 1.3 |
| Ex. 12 | 90.2 | 98.9 | 91.2 | 2.3 |
| Ex. 13 | 69.6 | 92.5 | 75.3 | 2.1 |
| Comp. Ex. 1 | hydrogen cyanide 90.6 | methanol 96.8 | hydrogen cyanide 93.6 | 1.5 |
| Comp. Ex. 2 | 81.2 | 93.8 | 86.6 | 4.2 |
| Comp. Ex. 3 | 83.7 | 98.9 | 84.6 | 4.8 |
| Comp. Ex. 4 | 62.4 | 73.6 | 84.8 | 7.1 |
| Comp. Ex. 5 | 80.7 | 94.2 | 85.7 | 2.1 |
| Comp. | 4.8 | 31.5 | 15.2 | 3.8 |

TABLE 1-continued

Ex. 6

*The desired product of Examples 1 to 6 and 9 to 13 is hydrogen cyanide and the starting material is methanol.
°The desired product of Comparative Examples 1 to 6 is hydrogen cyanide and the starting material is methanol.

EXAMPLE 14

A catalyst having the same composition as that of the catalyst of Example 13 was prepared in the same manner as in Example 13 with the exception of the following points.

A catalyst slurry in an amount of 4 times the amount of the slurry of Example 13 was prepared and divided into four portions. One portion thereof was left to stand for 20 minutes and then spray-dried. Another portion was left to stand for one hour and then spray-dried. Still another portion was left to stand for 3 hours and then spray-dried. The remaining portion was left to stand for 5 hours and then spray-dried. The resulting fine spherical particles (average particle diameter: 50μ) were calcined at 200° C. for 2 hours, at 500° C. for 2 hours and then at 850° C. for 3 hours.

It was found that iron antimonate was formed in all of the slurries before spray drying.

COMPARATIVE EXAMPLE 7

A catalyst having the same composition as that of the catalyst of Example 14 was prepared in the following manner.

(I) 1146.8 g of antimony trioxide powder was weighed.

(II) 60.0 g of electrolytic copper was added to 1680 ml of nitric acid (specific gravity: 1.38) and completely dissolved therein. The resulting copper nitrate solution was diluted with 2120 ml of pure water. 228.4 g of electrolytic iron powder was added thereto and dissolved therein.

(III) 5673.2 g of silica sol (20 wt % $SiO_2$) was weighed.

(IV) 5.56 g of ammonium paramolybdate was dissolved in 200 ml of pure water.

(V) 18.4 g of ammonium metavandate was dissolved in a mixed solution of 60 ml of 35% hydrogen peroxide solution and 200 ml of water.

(VI) 362.8 g of phosphoric acid (85 wt %) was weighed.

Silica sol (III) was added to the iron nitrate-copper nitrate solution (II). Subsequently, (I), (IV), (V) and (VI) in that order were added thereto. Aqueous ammonia (15 wt %) was added thereto with stirring to adjust the pH of the mixture to 0.5 and heated at 100° C. for one hour. The resulting slurry was divided into four portions. One portion was immediately spray-dried. One of another two portions was left to stand for 2 hours and then spray-dried, and the other was left to stand for 3 hours and then spray-dried. The remaining another portion was continuously heat-treated for 4 hours and then spray-dried. The resulting fine spherical particles obtained by spray-drying each of these portions (average particle diameter: 50μ) were calcined at 200° C. for 2 hours, at 500° C. for 2 hours and then at 850° C. for 3 hours. It was found that iron antimonate was not formed in any of these slurry portions before spray drying.

The results of activity tests of the catalysts obtained in Example 14 and Comparative Example 7, are shown in Table 2.

It is apparent from Table 2 that the activity and physical properties of the catalyst of Example 14 were not significantly varied even when the standing time of the slurry before spray drying was changed. It will be understood that according to the present invention, excellent catalysts can be industrially produced with good reproducibility.

On the other hand, the catalyst of Comparative Example 7 was greatly affected by the standing time of the slurry or the heat treating time in comparison with the catalyst of Example 14. In Comparative Example 7, the yield of the desired product was lowered, and particularly, physical properties such as bulk density and catalyst strength were deteriorated by a change in the standing time or the heat treatment time. Accordingly, it was difficult to produce excellent catalysts industrially with good reproducibility. Further, it was found that the process of Comparative Example 7 has disadvantages in that operability was poor. For example, the slurry readily caused the formation of precipitates and large amounts of deposits were formed on the wall of the spray drier during spray drying. Further, there were practical problems, since considerable amount of catalyst particles adhered to one another during calcination, caking was liable to be caused in static calcination and a stable fluidized bed could not be formed in fluidized bed calcination due to caking.

TABLE 2

| | Catalyst Composition (Atomic Ratio) | Heat Treatment of Slurry Temp. (°C.) Time (hr) | Standing Time of Slurry (hr.) | Final Calcination Temp. (°C.) | Rough Bulk Density (g/ml) | Activity Test Condition | | |
|---|---|---|---|---|---|---|---|---|
| | | | | | | Reaction | Reaction Temp. (°C.) | Contact Time (sec) |
| Ex. 14 | $Fe_{13}Sb_{25}P_{10}Mo_{0.1}-$ $V_{0.5}Cu_3O_{99.05}(SiO_2)_{60}$ | 100 4 | 0.2 | 850 | 1.17 | (1) | 430 | 1.0 |
| | | 100 4 | 2.0 | 850 | 1.17 | (1) | 430 | 1.0 |
| | | 100 4 | 3.0 | 850 | 1.18 | (1) | 430 | 1.0 |
| | | 100 4 | 4.0 | 850 | 1.17 | (1) | 430 | 1.0 |
| Comp. Ex. 7 | $Fe_{13}Sb_{25}P_{10}Mo_{0.1}-$ $V_{0.5}Cu_3O_{99.05}(SiO_2)_{60}$ | 100 1 | 0.2 | 850 | 1.00 | (1) | 430 | 1.0 |
| | | 100 1 | 2.0 | 850 | 0.90 | (1) | 430 | 1.0 |
| | | 100 1 | 3.0 | 850 | 0.89 | (1) | 430 | 1.0 |
| | | 100 4 | 0.2 | 850 | 0.77 | (1) | 430 | 1.0 |

| Result of Activity Test | | | |
|---|---|---|---|
| Yield of Desired Product (%) | Conversion of Starting Material (%) | Selectivity of Desired Product (%) | Attrition Loss (%)R |

TABLE 2-continued

| | Heat Treatment | Standing | Final | Rough | Activity Test Condition | |
|---|---|---|---|---|---|---|
| Ex. 14 | | | hydrogen cyanide 93.7 | methanol 100 | hydrogen cyanide 93.7 | 0.3 |
| | | | 93.8 | 100 | 93.7 | 0.4 |
| | | | 93.7 | 100 | 93.8 | 0.2 |
| | | | 93.9 | 100 | 93.7 | 0.3 |
| Comp. Ex. 7 | | | hydrogen cyanide 91.9 | methanol 99.4 | hydrogen cyanide 92.5 | 1.8 |
| | | | 90.7 | 98.9 | 91.7 | 2.5 |
| | | | 88.6 | 98.0 | 90.4 | 3.1 |
| | | | 87.9 | 99.1 | 88.7 | 5.2 |

While the invention has been described in detail and with reference to specific embodiments thereof, it will be apparent to one skilled in the art that various changes and modifications can be made therein without departing from the spirit and scope thereof.

What is claimed is:

1. An iron-antimony-phosphorus-containing metal oxide catalyst for catalytic oxidation, comprising a crystalline iron antimonate, said catalyst being represented by the following empirical formula:

$$Fe_aSb_bP_cX_dQ_eR_fO_g(SiO_2)_h$$

wherein X represents at least one element selected from the group consisting of V, Mo and W; Q represents at least one element selected from the group consisting of Li, Na, K, Rb, Cs, Be, Mg, Ca, Sr, Ba, Sc, Y, La, Ce, Pr, Nd, Sm, Th, U, Ti, Zr, Hf, Nb, Ta, Cr, Mn, Re, Co, Ni, Ru, Rh, Pd, Os, Ir, Pt, Cu, Ag, Au, Zn, Cd, Hg, Al, Ga, In, Tl, Ge, Sn and Pb; R represents at least one element selected from the group consisting of B, As, Bi, Se and Te; a, b, c, d, e, f, g and h each is an atomic ratio as follows:

(a = about 5 to 15
b = about 5 to 100
c = about 1 to 30
d = about 0 to 10
e = about 0 to 15
f = about 0 to 10
h = about 0 to 300 g is a number of oxygen atom as determined corresponding to the oxides formed by combining the above-mentioned components; the atomic ratio of P/Fe is at least 0.3; the atomic ratio of P/Sb is at least 0,1; and the atomic ratio of P/X is at least 1 when d>0.

2. The catalyst as claimed in claim 1, wherein Q represents at least one element selected from the group consisting of Li, Na, K, Rb, Cs, Mg, Ca, La, Ce, Ti, Zr, Nb, Ta, Cr, Mn, Re, Co, Ni, Cu, Ag, Zn, Al, Sn and Pb; and R represents at least one element selected from the group consisting of B, Bi and Te.

3. The catalyst as claimed in claim 1, wherein the atomic ratio of P/Fe is from 0.3 to 3 and the atomic ratio of P/Sb is from 0.1 to 3.

4. The catalyst as claimed in claim 1, wherein the atomic ratio of P/X is from 1 to 100.

5. A method for making an iron-antimony-phosphorus-containing metal oxide catalyst for catalytic oxidation, comprising a crystalline iron antimonate, said catalyst being represented by the following empirical formula:

$$Fe_aSb_bP_cX_dQ_eR_fO_g(SiO_2)_h$$

wherein X represents at least one element selected from the group consisting of V, Mo and W; Q represents at least one element selected from the group consisting of Li, Na, K, Rb, Cs, Be, Mg, Ca, Sr, Ba, Sc, Y, La, Ce, Pr, Nd, Sm, Th, U, Ti, Zr, Hf, Nb, Ta, Cr, Mn, Re, Co, Ni, Ru, Rh, Pd, Os, Ir, Pt, Cu, Ag, Au, Zn, Cd, Hg, Al, Ga, In, Tl, Ge, Sn and Pb; R represents at least one element selected from the group consisting of B, As, Bi, Se and Te; a, b, c, d, e, f, g and h each is an atomic ratio as follows:

a = about 5 to 15
b = about 5 to 100
c = about 1 to 30
d = about 0 to 10
e = about 0 to 15
f = about 0 to 10
h = about 0 to 300 g is a number of oxygen atom as determined corresponding to the oxides formed by combining the above-mentioned components; the atomic ratio of P/Fe is at least 0.3; the atomic ratio of P/Sb is at least 0.1; and the atomic ratio of P/X is at least 1 when d>0; comprising the steps of:

(a) preparing a slurry comprising a crystalline iron antimonate, a phosphorus component and any component contained in said catalyst selected from the group consisting of X, Q, R and SiO₂;

(b) drying said slurry to provide dry material; and (c) calcining said dried material to provide said metal oxide catalyst.

6. The method as claimed in claim 5, wherein in step (c) said dried material is calcined in air at a temperature of from about 200° C. to 950° C. for from about 0.5 to about 10 hours.

7. The method as claimed in claim 5, wherein said crystalline iron antimonate is prepared in a slurry in the absence of said phosphorus component.

8. The method as claimed in claim 7, wherein said iron antimonate is formed in said slurry by heat-treating an iron compound and an antimony compound at a temperature of about 40° to 150° C., and wherein said slurry has a pH of at most about 7 prior to said heat treatment.

9. The method as claimed in claim 5, wherein said crystalline iron antimonate is prepared in the absence of said phosphorus component by the steps of mixing an iron compound and an antimony compound and calcining the mixture obtained.

10. The method as claimed in claim 5, wherein in step (b) said slurry is spray-dried to form fine spherical particles, and said calcined dry material from step (c) is a fluidized bed catalyst.

* * * * *